United States Patent
Rasmussen et al.

(10) Patent No.: US 10,195,015 B2
(45) Date of Patent: Feb. 5, 2019

(54) IMPLANTABLE MEDICAL DEVICE

(71) Applicant: COOK MEDICAL TECHNOLOGIES LLC, Bloomington, IN (US)

(72) Inventors: Erik Rasmussen, Slagelse (DK); Bent Oehlenschlaeger, Lille Skensved (DK); Kim Moegelvang Jensen, Frederiksberg (DK); Jesper Schade Petersen, Holmegaard (DK)

(73) Assignee: Cook Medical Technologies LLC, Bloomington, IN (US)

(*) Notice: Subject to any disclaimer, the term of this patent is extended or adjusted under 35 U.S.C. 154(b) by 3 days.

(21) Appl. No.: 15/150,987

(22) Filed: May 10, 2016

(65) Prior Publication Data

US 2016/0256257 A1 Sep. 8, 2016

Related U.S. Application Data

(63) Continuation of application No. 12/849,470, filed on Aug. 3, 2010, now abandoned.

(30) Foreign Application Priority Data

Aug. 11, 2009 (GB) .................................. 0914045.0

(51) Int. Cl.
*A61F 2/07* (2013.01)
*A61F 2/844* (2013.01)
(Continued)

(52) U.S. Cl.
CPC ................ *A61F 2/07* (2013.01); *A61F 2/844* (2013.01); *A61F 2/90* (2013.01); *A61F 2/86* (2013.01);
(Continued)

(58) Field of Classification Search
CPC ...... A61F 2220/0075; A61F 2002/9505; A61F 2250/0098; A61F 2/07
See application file for complete search history.

(56) References Cited

U.S. PATENT DOCUMENTS 5,282,824 A  2/1994 Gianturco
5,897,589 A  4/1999 Cottenceau et al.
(Continued)

FOREIGN PATENT DOCUMENTS

EP  0857471 A3  8/1998
WO  WO 99/44535 A1  9/1999
(Continued)

OTHER PUBLICATIONS http://dictionary.reference.com/browse/coiled printed Jun. 8, 2011.
(Continued)

*Primary Examiner* — Brian Pellegrino
(74) *Attorney, Agent, or Firm* — Brinks Gilson & Lione

(57) ABSTRACT

A stent graft includes a tubular graft element to which there are attached a plurality of stent rings. The stent rings are formed of a plurality of stent struts arranged in a zig-zag arrangement with alternating peaks and valleys. The end-most stent is located at the proximal end of the graft tube. Between adjacent peaks of the end most stent, there is provided a series of bridging elements. These are preferably formed of Nitinol wire and to be substantially more flexible than the stent struts. The bridging elements extend in the region of graft material between adjacent stent peaks and are attached to the graft material, for example by suturing. The bridging elements are substantially more flexible than the stent ring and therefore impart little opening force on the graft material in comparison to the force produced by the stent ring. However, the bridging elements impart enough force on the flaps of graft material between the peaks of the (Continued)

stent ring keep these flaps open, that is against the vessel wall. The bridging elements can provide integral barbs.

12 Claims, 3 Drawing Sheets

(51) Int. Cl.
*A61F 2/90* (2013.01)
*A61F 2/86* (2013.01)
*A61F 2/848* (2013.01)
*A61F 2/89* (2013.01)

(52) U.S. Cl.
CPC ........... *A61F 2/89* (2013.01); *A61F 2002/075* (2013.01); *A61F 2002/8483* (2013.01); *A61F 2210/0014* (2013.01); *A61F 2220/0058* (2013.01); *A61F 2220/0075* (2013.01); *A61F 2310/00023* (2013.01)

(56) References Cited

U.S. PATENT DOCUMENTS

| | | | |
|---|---|---|---|
| 5,964,798 A | 10/1999 | Imran | |
| 6,004,347 A | 12/1999 | McNamara et al. | |
| 6,231,598 B1 | 5/2001 | Berry et al. | |
| 6,331,191 B1 | 12/2001 | Chobotov | |
| 6,395,019 B2 | 5/2002 | Chobotov | |
| 6,454,799 B1 | 9/2002 | Schreck | |
| 6,464,723 B1 | 10/2002 | Callol | |
| 6,773,455 B2 | 8/2004 | Allen et al. | |
| 7,022,132 B2 * | 4/2006 | Kocur | A61F 2/90 623/1.11 |
| 7,175,652 B2 | 2/2007 | Cook et al. | |
| 7,354,450 B2 | 4/2008 | Bicek et al. | |
| 7,413,573 B2 * | 8/2008 | Hartley | A61F 2/07 623/1.13 |
| 7,462,192 B2 * | 12/2008 | Norton | A61F 2/90 623/1.53 |
| 7,758,626 B2 * | 7/2010 | Kim | A61F 2/07 606/108 |
| 8,691,321 B2 * | 4/2014 | Cottone | A61F 2/915 264/150 |
| 2001/0032010 A1 | 10/2001 | Sandock | |
| 2004/0098092 A1 | 5/2004 | Butaric et al. | |
| 2004/0111146 A1 | 6/2004 | McCullagh | |
| 2005/0131525 A1 * | 6/2005 | Hartley | A61F 2/07 623/1.15 |
| 2005/0143801 A1 | 6/2005 | Aboul-Hosn | |
| 2005/0267560 A1 | 12/2005 | Bates | |
| 2007/0043432 A1 | 2/2007 | Perouse | |
| 2007/0067016 A1 | 3/2007 | Jung | |
| 2007/0100432 A1 | 5/2007 | Case et al. | |
| 2007/0179591 A1 | 8/2007 | Baker et al. | |
| 2007/0191929 A1 | 8/2007 | Osborne et al. | |
| 2008/0051868 A1 * | 2/2008 | Cottone | A61F 2/91 623/1.11 |
| 2008/0262593 A1 | 10/2008 | Ryan et al. | |
| 2010/0057195 A1 | 3/2010 | Roeder et al. | |
| 2010/0211155 A1 | 8/2010 | Swanson et al. | |

FOREIGN PATENT DOCUMENTS

| | | |
|---|---|---|
| WO | WO 01/89421 A2 | 11/2001 |
| WO | WO 02/060344 A2 | 8/2002 |
| WO | WO 2004/105853 A1 | 12/2004 |

OTHER PUBLICATIONS

International Search Report and Written Opinion for PCT/US2010/044244, dated Oct. 6, 2010, 7 pages.
Examination Report for EP 10742670.2 dated Jul. 15, 2014, 4 pages.
Combined Search and Examination Report for GB 0914045.0 dated Dec. 14, 2009, 4 pages.

* cited by examiner

IMPLANTABLE MEDICAL DEVICE

RELATED APPLICATIONS

The present patent document is a continuation of application Ser. No. 12/849,470, filed Aug. 3, 2010, which claims the benefit of priority to United Kingdom Patent Application No. 0914045.0, filed Aug. 11, 2009, and entitled "IMPLANTABLE MEDICAL DEVICE," the entire contents of each of which are incorporated herein by reference.

BACKGROUND

1. Technical Field Text

The present invention relates to an implantable medical device, such as a stent graft. In the preferred embodiment, the device includes a plurality of bridging elements coupled at a proximal and/or distal end of the medical device.

2. Background

In the medical field it is now commonplace to use stent grafts and other implantable medical devices to treat a variety of medical conditions such as aneurysms, dissections, occlusions and the like. Stent grafts are generally formed of a tubular member of graft material (which may or may not be bifurcated or have side branches) and one or more stents provided on the graft member to retain this in an open position. The stents may be located on the inside or the outside of the graft member, or both, as desired in connection with the particular medical device or medical application. Some vena cava filters are also in the form of a stent graft, that is have a graft element which is supported by a stent structure. The teachings herein apply equally to such vena cava filters.

Stents used in stent grafts come in a variety of forms, the most common of which is a stent ring formed of a series of strut elements arranged in a zig-zag or sinusoidal manner. The advantage of a zig-zag or sinusoidal stent is that this can be readily compressed onto an introducer for endoluminal deployment of the stent graft. Furthermore, this arrangement of the strut elements gives the stent a good expansion strength, that is the enable the stent to expand and press against a vessel wall in so doing to support the graft member in an open configuration and to hold the medical device in position.

Zig-zag stents of such a nature can be considered to be formed of a plurality of stent struts which are coupled to one another at their ends to provide a structure having a plurality of peaks and valleys at the junctions between adjacent stent struts.

Greater compressibility and flexibility of the medical device can be achieved with a zig-zag structure which is more open (that is, where the angle between adjacent and connected stent struts is relatively greater). This is particularly useful for stent grafts which need to be compressed to a very small diameter for introduction and implantation into a patient, as well as in cases where the stent graft needs to remain flexible as a result of the physiology of the lumen into which the stent graft is to be implanted.

There is typically provided an end stent located at the proximal end of the stent graft (that is the end which is located upstream or closer to the heart relative to the remainder of the stent graft), in order to keep this end open. There is commonly also provided a stent at least at the distal end of the stent graft and generally also one or more stents in intermediate positions along the graft member.

The proximal end of the stent graft needs to be retained fully open so as to ensure that this properly seals against the internal walls of the patient's vessel and must also be retained in the correct position in the vessel, both during and after deployment. Where the end most stent is of a zig-zag or sinusoidal structure, particularly a relatively open structure to increase the flexibility and compressibility of the stent graft, this can lead to unsupported flaps of graft material between adjacent peaks of the stent. These flaps of graft material will tend to be urged radially inwardly towards the centre of the lumen as a result of blood flow impinging upon the proximal end of the stent graft. This will result in an incomplete seal of the graft material to the inner vessel wall. When this endoleak, blood leakage occurs, there is the risk of: a) an endoleak, in which blood can flow passed the device and the lumen wall; b) migration of the stent graft with the patient's lumen; and c) also premature wear and tear of the stent graft caused by the flapping of the graft material.

It is known to locate at the proximal end of the graft member one or more bare stents which extend beyond the extremity of the graft member and which can support the proximal end of the graft member, particularly those portions not supported by the other stents of the stent graft to urge these portions against the vessel walls. Bare stents of this nature can also be provided with barbs which anchor into the vessel wall.

Although bare stents have particular uses in some medical applications, they are not suitable in a number of circumstances as they can cause erosion of the vessel wall. Bare stents are generally not ideal in very tortuous anatomies. They can in some circumstances also reduce the flexibility of the stent graft assembly.

Other forms of stent located at the proximal end of the stent graft and specifically designed to overcome the problem of support of its proximal end will impair the compressibility of the stent graft as well as, in some circumstances, its flexibility in situ.

BRIEF SUMMARY

The present invention seeks to provide an improved implantable medical device.

According to an aspect of the present invention, there is provided an implantable medical device including a tubular graft member; at least one stent provided on the graft member proximate an end thereof, wherein the stent is formed from a plurality of struts coupled together at their ends in the form of a stent ring having peaks and valleys, the struts of the stent being formed of a flexible material to allow the stent to be compressed and to expand, wherein the struts have a first flexibility; and a plurality of bridging elements located between adjacent peaks formed by the struts of said stent, said bridging elements being coupled to the struts and extending towards and proximate said end of said graft element; said bridging elements having a second flexibility, wherein second flexibility is greater than said first flexibility; wherein said bridging elements produce in use an expansion force urging graft material of said graft element in a graft opening direction, wherein the opening force produced by said bridging elements is less than an opening force produced by said stent ring.

The structure of implantable medical device taught herein retains the advantages of a relatively open stent structure to maintain flexibility and compressibility of the medical device and yet provides a mechanism for urging all of the portions of the proximal end of the graft member properly against a vessel wall to maintain patency with the vessel wall and to prevent any parts of the graft member from falling into the lumen of the vessel and thereby to lose the seal against the vessel wall. This can be achieved without compromising in any significant way the flexibility and compressibility of the implantable medical device.

Preferably, the bridging elements are located within the extent of the graft member. In other words, the bridging elements do not extend beyond the graft member, as does a bare stent. Such a structure is advantageous when the device is to be deployed in a very tortuous vessel. With this particular arrangement, it is also possible to protect the vessel wall by ensuring that the metal or metallic components of the device are covered by graft material, thus avoiding the risk of trauma and/or erosion of the vessel wall of the type which can occur with devices provided with bare stents.

In a preferred embodiment, the opening force produced by the bridging elements is between around 10% to around 75%, more preferably, around 10% to around 50% or around 10% to around 40%, of the opening force produced by the stent ring. The purpose of the bridging elements is not to provide an expansion force against the vessel walls of the type produced by the stent but simply to maintain the otherwise loose parts of the graft material open. Therefore, in the preferred embodiment, the majority of the expansion force is generated by the stent, with the bridging elements contributing only a minor part of the opening force.

In the preferred embodiment, the bridging elements produce an opening force which is in the region of 50% of the opening force produced by the stent ring, in other embodiments the force may be around 20% or around 30%.

In the preferred embodiment, the bridging elements are formed from a length of wire. Advantageously, the bridging elements are coupled to the stent by wrapping the wire around the struts. Most preferably, the bridging elements include at least one barb element, this advantageously being formed by an end of the wire or wire-like element forming the bridging elements.

It is preferred that the bridging elements are formed of a shape memory material such as Nitinol. It is also preferred that the stent or stents of the stent graft are formed of a self-expandable material. It is envisaged, nevertheless, that the bridging elements and/or stent or stents of the stent graft could be formed of a balloon expandable material.

BRIEF DESCRIPTION OF THE DRAWINGS

Embodiments of the present invention are described below, by way of example only, with reference to the accompanying drawings, in which.

DETAILED DESCRIPTION OF THE DRAWINGS AND THE PRESENTLY PREFERRED EMBODIMENTS

Figure 1:
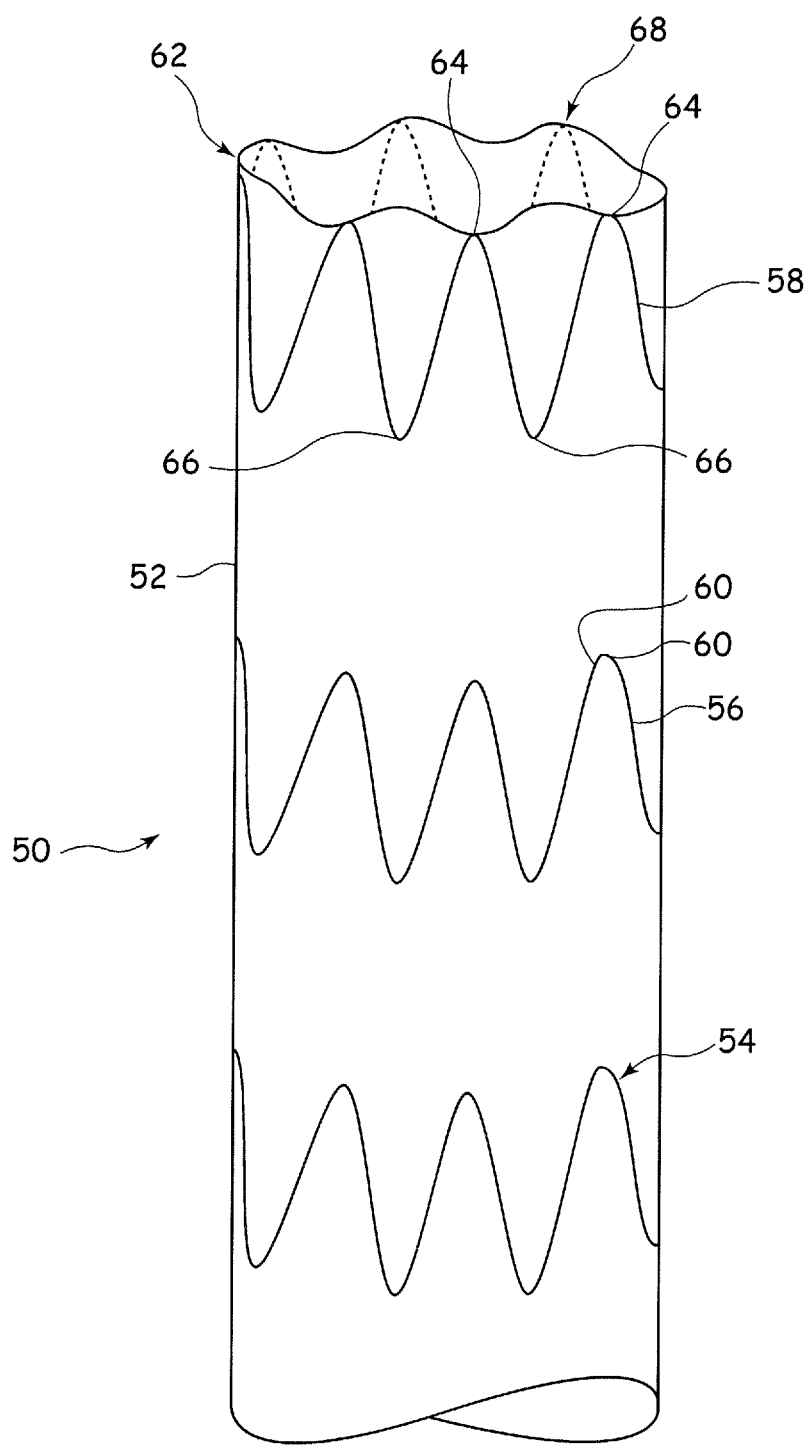
FIG. 1 shows in schematic form a side elevational view a prior art stent graft assembly.

Referring to FIG. 1, there is shown in schematic form an example of prior art stent graft 50 which includes a tubular member 52 formed of graft material and attached thereto a plurality of stents 54-58. The stents 54-58 are of a known annular form and have a zig-zag shape, formed by a plurality of stent struts 60 coupled together in an alternating peak and valley arrangement. The stent 58 at the proximal end 62 of the graft member 52 is intended to maintain the proximal end 62 of the graft member open. It can be seen that the stent 58 has a plurality of peaks 64 at or adjacent the proximal end 62 of the graft member, and a plurality of valleys 66 at the other end of the stent 58. In locations between adjacent peaks 64 of the stent 58, the graft material is unsupported. As a result, and in particular in light of the fact that in situ the stent graft 50 is typically not fully expanded, there are formed a plurality of loose flaps 68 of graft material.

Figure 2:
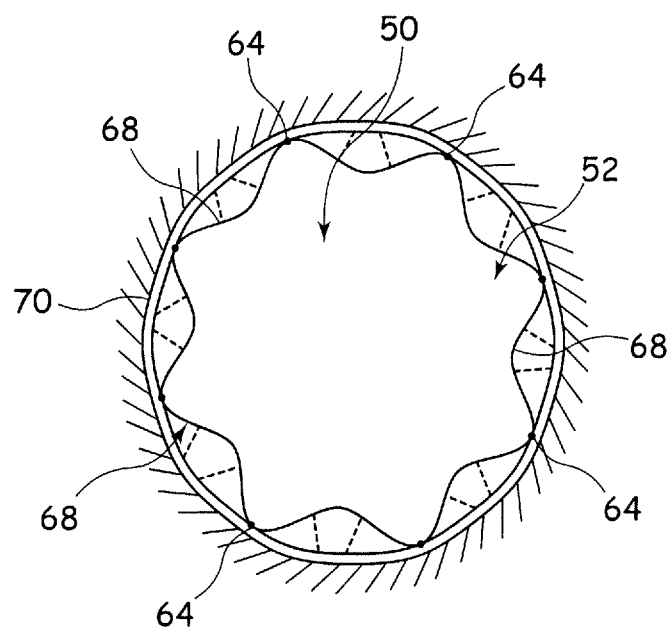
FIG. 2 shows a plan view of the stent graft assembly of FIG. 1 located within a vessel.

Referring to FIG. 2, this shows the stent graft 50 located within a vessel 70 and in a configuration in which the stent graft 50 is expanded against the vessel wall. As is normal in such circumstances, the stent graft 50 is not expanded to its maximum extent and remains slightly compressed. This allows it to maintain an expansion force and thus to press the stent graft 50 against the walls of the vessel 70. The flaps 68 at the proximal end 62 of the stent graft 50, being unsupported, will tend to be pushed inwardly towards the interior of the vessel 70 as a result of fluid pressure in the vessel. As a consequence of this, the flaps 68 will form pockets between the vessel walls 70 and the interior of the stent graft 50, which will be filled with blood flowing into the stent graft 5. In practice, the flaps 68 will vibrate in the flow of blood.

The formation of the flaps 68 prevents a proper seal being formed between the proximal end 62 of the stent graft 50 and the vessel walls 70. Moreover, the constant vibration or movement of the flaps will result in premature wear of the graft material 52.

As explained above, providing an end stent 58 with a tighter strut structure will reduce the compressibility of the stent 58 and the flexibility of the stent graft 50 in situ. Any other form of stent structure will again compromise the compressibility and flexibility of the stent graft 50. Similarly, providing bare stents at the proximal end 62 of the stent graft is disadvantageous in some applications.

Figure 3:
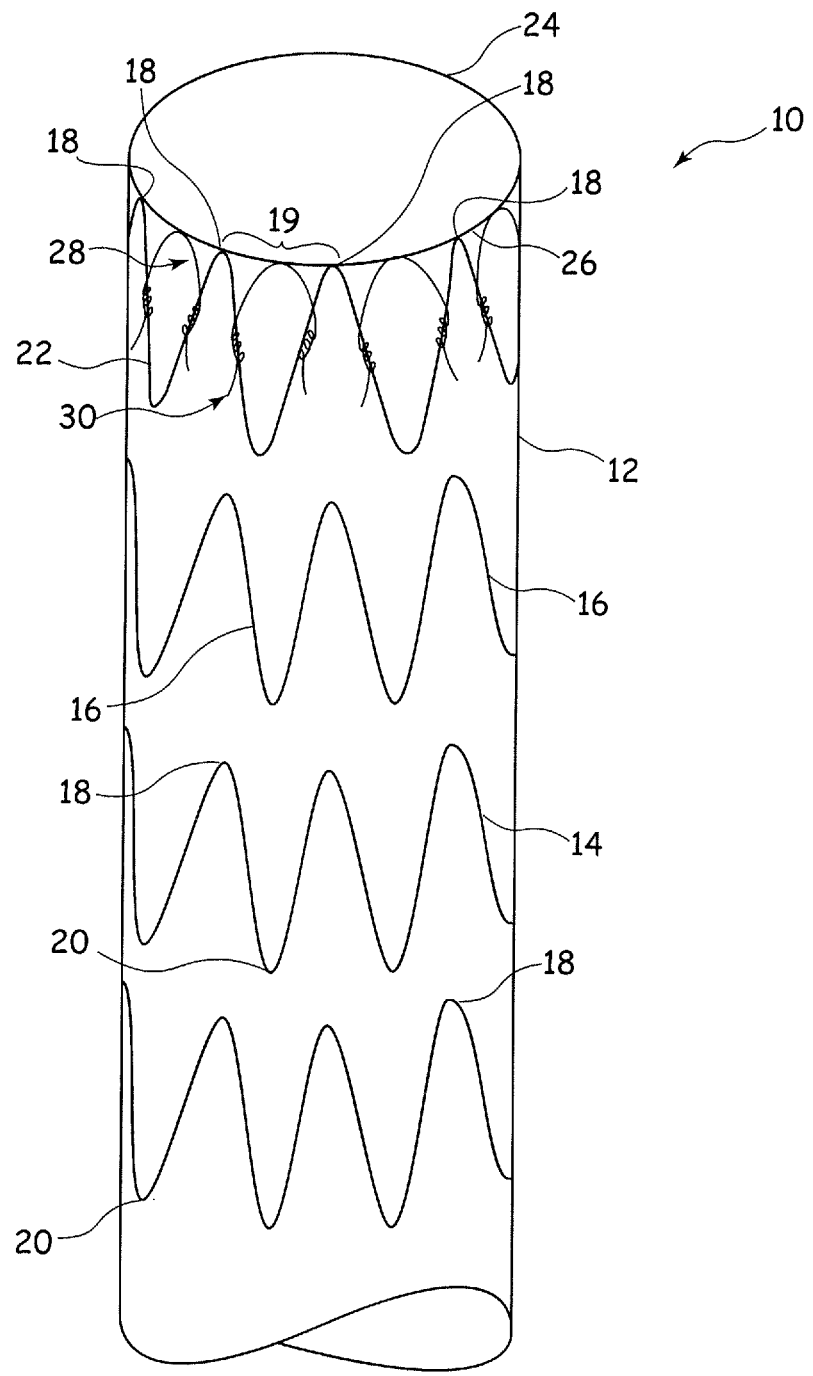
FIG. 3 is a side elevational view, in schematic form, of a preferred embodiment of stent graft assembly.

FIG. 3 shows in schematic form an embodiment of stent graft assembly in accordance with the present invention. The embodiment shown is of a tubular stent graft assembly 10, although the teachings herein can be applied to other forms of stent graft assembly, for example bifurcated stent grafts, stent grafts with side branches, modular stent grafts and the like. The teachings herein can also be applied to other forms of implantable medical devices which include a flexible element or covering.

Referring to FIG. 3, the embodiment of stent graft assembly 10 shown includes a tubular graft member 12, of conventional form, to which there attached a plurality of stent rings 14. The stent rings 14 are formed of a plurality of stent struts 16 which are arranged in what could be described as a zig-zag arrangement in which the stent struts form alternating peaks 18 and valleys 20. The end-most stent 22 is located adjacent the proximal end 24 of the graft member 12 and in practice in an upstream direction in a patient's vessel. The struts 16 of the stent rings 14 have an angle between adjacent struts which is relatively open in order to provide good compressibility and flexibility of the stent graft 10. Between adjacent peaks 18 of the end most stent 22 there is provided graft material which is unsupported by the structure of the stent 22. The regions of graft material between adjacent peaks 18 of the endmost stent 22 are denoted by the reference numeral 19 in FIG. 3.

Located in each region 19 between adjacent peaks 18 there is provided a bridging element 28. The bridging elements 28 can be seen in enlarged form in FIG. 4.

In the preferred embodiment the bridging elements are made of a wire or wire-like material and are curved, as shown, to extend into the gap 19 between adjacent peaks 18 of the struts forming the stent ring 22. The bridging elements 28 may be coupled to the graft material 12 by a suture, bonding or any other suitable coupling mechanism, so as to be able to apply pressure on the graft material in the zone 19. In embodiments in which the bridging elements 28 are located in the inside of the graft element 12, they need not be specifically coupled to the graft material 12 as the expansion of the bridging elements 28 will push against the graft material 12 from the inside and thus push the portions of graft material in the zones 19 outwardly, in practice against the vessel wall. In applications where the bridging elements 28 are positioned on the outside of the graft material 12 they would typically be connected to the graft material, for instance by bonding or suturing.

Figure 4:
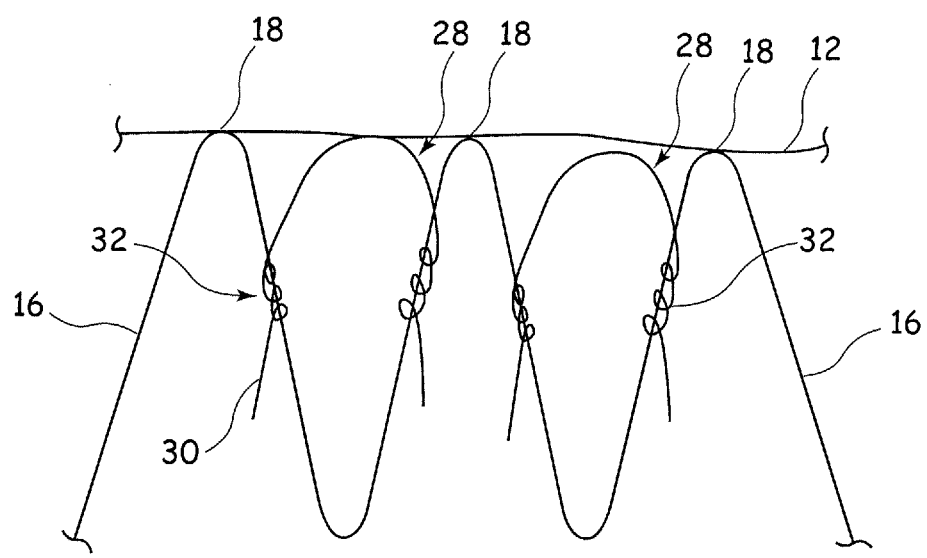
FIG. 4 is an enlarged view of a section of the stent graft assembly of FIG. 3.

The bridging elements in the embodiment of FIG. 4 are wrapped around adjacent struts 16 of the end most stent 22, typically simply by coiling these around the struts 16. Such wrapping fixes the bridging elements 28 to the stent graft structure 10 and in practice allow the bridging elements 28 to expand with the stent 22. The stent 22 will provide a support against which the bridging elements 28 press when these expand by their own expansion force in order to push the portions of the graft material 12 in the zones 19 in an outwardly direction.

It is envisaged that in some embodiments the bridging elements 28 would also or in the alternative be sutured to the struts 16 and/or to the graft member 12 in a location adjacent the strut 16 of the stent 22.

It will be seen in FIGS. 3 and 4 that the bridging elements 28 and in particular the curved portion of these lying in the zone 19, do not extend beyond the end of the graft material 12. This enables the graft material 12 to act as a protecting covering over the bridging elements 28 and thus as an interstice or protective layer preventing direct contact of the bridging elements 28 to the interior of the vessel wall 70, thereby avoiding some of the disadvantages of bare stents.

In the embodiment of FIGS. 3 and 4, the bridging elements 28 have free ends 30 which extend beyond the couplings 32 on the struts 16. These free ends 30 can in practice be pin-like and are able to constitute barbs which in practice will extend radially out of the stent graft assembly 10 and in particular beyond the radial extent of the graft member 12. These barbs 30 are able to be implanted in a vessel wall 70 so as to fix the stent graft assembly 10 within the vessel 70. The barbs 30 would have a structure and function analogous to that of known barbs. The advantage, however, is that the barbs 30 are simple extensions of the bridging elements 28 and are thus conveniently manufactured and assembled to the stent graft 10.

The bridging elements 28 are preferably substantially more flexible than the stent 22. By more flexible, it is meant that the bridging elements 28 will generate a substantially lower contraction resistance and expansion force relative to those generated by the stent 22. In the preferred embodiment, the bridging elements 28 produce an expansion force which is between around 10% to around 75% of the expansion force produced by the stent 22, more preferably between around 10% to around 50% or around 10% to around 40%. In the preferred embodiment, these forces generated by the bridging elements 28 are around 50% (or around 20% or around 30%) of the equivalent forces produced by the stent 22. Making the bridging elements 18 weaker can be achieved by using a more flexible material for the bridging elements 28 compared to the material of the stent 22 and/or by using a material of smaller cross sectional area. In some embodiments, the bridging elements 28 could be made of the same material as the material of the stent 22 (for example Nitinol or other shape memory material) but have a cross-sectional area which is substantially less than the cross-sectional area of the strut 16 of the stent 22. This cross sectional area could be between around 10% to around 75% (or around 10% to around 50% or around 10% to around 40%) of the cross sectional area of the strut 16 but preferably in the region of 50%, 20% or 30% or so.

Having bridging elements 28 which are substantially more flexible than the stent 22 ensures that the bridging elements 28 provide at most only a minimal effect on the compressibility and flexibility of the stent graft 10 and most preferably only a minimal variation of that compressibility and flexibility compared to an assembly 10 having no bridging elements 28 and no other mechanism for supporting the graft material in the zone 19. Thus, the bridging elements 28, in the preferred embodiment, do not impair these characteristics of the stent graft 10 but have the function of ensuring that the proximal end 24 of the graft member 12 is properly pressed against the walls of the vessel 70 and thus provides a proper seal and patency of the stent graft 10 to the vessel wall. Thus, a stent graft with improved compressibility and improved flexibility can be provided while still ensuring proper sealing of the proximal end 24 of the stent graft to the vessel.

The embodiment of FIGS. 3 and 4 show bridging elements 28 located at the endmost stent 22. It will be appreciated that bridging elements 28 can be provided on the other stents 14 of the stent graft assembly 10, in particular at other ends of the stent graft (for example, at the distal end or at the ends of branches or bifurcations of the stent graft). Similarly, bridging elements 28 can be provided at the stents of different modules of a modular stent graft assembly.

Although the bridging elements 28 are shown to be wrapped around the strut 16 of the endmost stent 22, they could be fixed to the stent 22 in other ways, such as by bonding, soldering, welding or the like. Similarly, the bridging elements 28 could be coupled to the graft material, for example by suturing.

The invention claimed is:

1. A stent graft comprising:
a tubular graft having a first end opening, a second end opening, a first end opening edge, a lumen between the first end opening and the second end opening, and an intermediate region between the first end opening and the second end opening;
an end-most zig zag stent disposed on tubular graft adjacent the first end opening, the zig zag stent comprising:
a plurality of first apices extending circumferentially about the tubular graft and abutting the first end opening edge and defining a region of graft material between adjacent first apices that is unsupported by the end most zig zag stent,
a plurality of second apices extending circumferentially about the tubular graft and extending away from the first apices toward the intermediate region of the tubular graft,
a plurality of struts, with each strut extending between one of the first apices and one of the second apices;
and
a plurality of discrete wire-like bridges, each of the plurality of wire-like bridges having:
a first end engaging a first strut of the plurality of struts, a second end engaging a second strut of the plurality of struts directly circumferentially adjacent the first strut, and an intermediate section between the first and second ends, wherein the intermediate section comprises a curve extending proximally between directly adjacent first apices to span the unsupported region of graft material of the tubular graft between the directly adjacent first apices, wherein the proximally extending curve of each of the plurality of wire-like bridges aligns with and abuts the first end opening edge of the tubular graft between the directly adjacent first apices to support the unsupported region of graft material between directly adjacent apices at the first end opening edge, wherein none of the wire-like bridges is directly connected to another of the wire-like bridges, and wherein each of the wire-like bridges is more flexible than the zig-zag stent wire-like bridges are located entirely between the first end opening and the second end opening of the tubular graft, such that the wire-like bridges do not extend beyond the first end opening edge of the tubular graft and has less of an expansion force than the zig-zag stent.

2. The stent graft of claim 1, wherein the expansion force produced by the wire-like bridges is between 10% to 75% of the expansion force produced by the end-most zig zag stent.

3. The stent graft of to claim 1, wherein the expansion force produced by the wire-like bridges is in the region of 50% of the expansion force of the end-most zig-zag stent.

4. The stent graft of claim 1, wherein the wire-like bridges have a transverse cross-sectional area of 10% to 75% of a cross-sectional area of the struts of the end-most zig-zag stent.

5. The stent graft of claim 1, wherein the wire-like bridges have a transverse cross-sectional area of around 10%-75% of a thickness of the struts of the end-most zig-zag stent.

6. The stent graft of claim 1, wherein the wire-like bridges is a length of metal wire.

7. The stent graft of claim 1, wherein the first and second ends of each of the wire-like bridges is a free end and wherein the free ends are coils disposed around the stent struts.

8. The stent graft of claim 1, wherein the wire-like bridges are provided with at least one barb element.

9. The stent graft of claim 8, where each wire-like bridge includes two barb structures.

10. The stent graft of claim 1, wherein the wire-like bridges are disposed entirely inside the lumen of the tubular graft.

11. The stent graft of claim 1, wherein no portion of the wire-like bridges extends beyond the first end opening edge of the tubular graft.

12. A stent graft comprising:

a tubular graft having a first end opening, a second end opening, a first end opening edge, a lumen between the first end opening and the second end opening, and an intermediate region between the first end opening and the second end opening;

an end-most zig zag stent disposed on tubular graft adjacent the first end opening and configured to lie upstream in a patient's vessel, the end-most zig zag stent comprising:

a plurality of first apices extending circumferentially about the tubular graft and abutting the first end opening edge and defining an unsupported region of graft material between adjacent first apices, a plurality of second apices extending circumferentially about the tubular graft and extending away from the first apices toward the intermediate region of the tubular graft, a plurality of struts, with each strut extending between one of the first apices and one of the second apices; and a plurality of discrete wire-like bridges, each of the plurality of wire-like bridges having:

a first end engaging a first strut, a second end engaging a second strut directly circumferentially adjacent the first strut, and an intermediate section between the first and second ends, wherein the intermediate section comprises a curve extending proximally between directly adjacent first apices to span the unsupported region of graft material of the tubular graft between the directly adjacent first apices, wherein the proximally extending curve of each of the plurality of wire bridges aligns with and abuts the first end opening edge of the tubular graft between the directly adjacent first apices to support the unsupported region of graft material between directly adjacent apices at the first end opening edge, wherein no portion of the wire bridges extends beyond the first end opening edge of the tubular graft, wherein none of the wire-like bridges is directly connected to another of the wire-like bridges, and wherein each of the wire bridges is more flexible than the end-most zig-zag stent and has less of an expansion force than the end-most zig-zag stent.

* * * * *